(12) United States Patent
Yaman et al.

(10) Patent No.: US 10,350,082 B2
(45) Date of Patent: Jul. 16, 2019

(54) EXPANDABLE CAGE

(71) Applicant: TOBB EKONOMI VE TEKNOLOJI UNIVERSITESI, Ankara (TR)

(72) Inventors: Mesut Emre Yaman, Ankara (TR); Teyfik Demir, Ankara (TR); Tolga Tolunay, Ankara (TR)

(73) Assignee: TOBB EKONOMI VE TEKNOLOJI UNIVERSITESI, Ankara (TR)

( * ) Notice: Subject to any disclaimer, the term of this patent is extended or adjusted under 35 U.S.C. 154(b) by 0 days.

(21) Appl. No.: 15/770,339

(22) PCT Filed: Oct. 24, 2016

(86) PCT No.: PCT/TR2016/000149
§ 371 (c)(1),
(2) Date: Apr. 23, 2018

(87) PCT Pub. No.: WO2017/074277
PCT Pub. Date: May 4, 2017

(65) Prior Publication Data
US 2018/0280155 A1    Oct. 4, 2018

(30) Foreign Application Priority Data

Oct. 26, 2015   (TR) .............................. a 2015 13364

(51) Int. Cl.
*A61F 2/44*   (2006.01)
*A61F 2/30*   (2006.01)

(52) U.S. Cl.
CPC ............ *A61F 2/4425* (2013.01); *A61F 2/442* (2013.01); *A61F 2002/3052* (2013.01); *A61F 2002/30153* (2013.01); *A61F 2002/30492* (2013.01)

(58) Field of Classification Search
CPC ............................................ A61F 2/442–4425
See application file for complete search history.

(56) References Cited

U.S. PATENT DOCUMENTS

| | | | | |
|---|---|---|---|---|
| 2008/0021556 A1* | 1/2008 | Edie | .......................... | A61F 2/44 623/17.11 |
| 2008/0058931 A1* | 3/2008 | White | ....................... | A61F 2/44 623/17.11 |
| 2009/0076610 A1* | 3/2009 | Afzal | ...................... | A61F 2/442 623/17.16 |

(Continued)

*Primary Examiner* — Eduardo C Robert
*Assistant Examiner* — Michelle C Eckman
(74) *Attorney, Agent, or Firm* — Egbert Law Offices, PLLC

(57) ABSTRACT

An expandable cage which is placed between the vertebrae, is moveable when preferred, closes the opening between the vertebrae upon being moved, and hence can be integrated in any intervertebral opening. The expandable cage has at least one body with at least one space and at least one rib; at least one moveable part which is located inside the body and has at least one bearing area, at least one base, and at least one nail, the moveable part being moved unilaterally by the balloon; at least one balloon which applies the force required to be applied on the base of the moveable part for ensuring unilateral movement of the moveable part; at least one hole through which the balloon can pass; and at least one compression element which supplies the required fluid to the balloon.

5 Claims, 1 Drawing Sheet

(56) References Cited

U.S. PATENT DOCUMENTS

| | | | | |
|---|---|---|---|---|
| 2009/0182343 A1* | 7/2009 | Trudeau | A61F 2/4657 | 606/102 |
| 2009/0270987 A1* | 10/2009 | Heinz | A61F 2/44 | 623/17.16 |
| 2010/0057204 A1* | 3/2010 | Kadaba | A61F 2/442 | 623/17.12 |
| 2010/0063510 A1* | 3/2010 | Arlet | A61F 2/44 | 606/93 |
| 2010/0185288 A1* | 7/2010 | Carls | A61F 2/442 | 623/17.11 |
| 2010/0268340 A1* | 10/2010 | Capote | A61F 2/44 | 623/17.12 |
| 2010/0268341 A1* | 10/2010 | Dvorak | A61F 2/44 | 623/17.12 |
| 2011/0092859 A1* | 4/2011 | Neubardt | A61B 5/1077 | 600/594 |
| 2011/0130835 A1* | 6/2011 | Ashley | A61F 2/442 | 623/17.11 |
| 2011/0230970 A1* | 9/2011 | Lynn | A61F 2/442 | 623/17.16 |
| 2011/0257688 A1* | 10/2011 | Miller | A61F 2/44 | 606/279 |
| 2011/0257745 A1* | 10/2011 | Miller | A61F 2/44 | 623/17.11 |
| 2012/0101576 A1* | 4/2012 | Dewey | A61F 2/44 | 623/17.11 |
| 2012/0116516 A1* | 5/2012 | Aflatoon | A61F 2/442 | 623/17.16 |
| 2012/0136399 A1* | 5/2012 | Seifert | A61B 17/1617 | 606/86 A |
| 2012/0143335 A1* | 6/2012 | Lee | A61F 2/44 | 623/17.11 |
| 2012/0271419 A1* | 10/2012 | Marik | A61F 2/4425 | 623/17.12 |
| 2012/0296433 A1* | 11/2012 | Farin | A61F 2/442 | 623/17.16 |
| 2013/0131808 A1* | 5/2013 | Suh | A61F 2/30721 | 623/17.16 |
| 2014/0358246 A1* | 12/2014 | Levy | A61F 2/442 | 623/23.47 |
| 2015/0257894 A1* | 9/2015 | Levy | A61F 2/442 | 623/17.15 |
| 2018/0280155 A1* | 10/2018 | Yaman | A61F 2/4425 | |
| 2018/0296357 A1* | 10/2018 | Yaman | A61F 2/442 | |
| 2018/0318105 A1* | 11/2018 | Yaman | A61F 2/44 | |

* cited by examiner

EXPANDABLE CAGE

TECHNICAL FIELD

The present invention relates to an expandable cage which is placed between the vertebrae and moves in one direction, i.e. unilaterally, by means of a balloon.

PRIOR ART

Discs made of articular fibrocartilage and allowing the vertebrae to move easily with respect to one another are present between human vertebrae. Two adjacent vertebrae can easily move relative to one another thanks to said discs, in six degrees of freedom. Discs are present between all successive vertebrae, thereby allowing a limited movement of the vertebral column. In case damage occurs in the vertebrae or vertebral column due to an accident, a tumor incidence, or old age, a part of the disc may be dislocated and apply pressure on the nerve roots and/or the spinal cord. In such cases, the so-called discectomy procedure is performed in which the whole, or a part of the disc is removed surgically. There remains a space between the vertebrae subsequent to discectomy. Said space results in a decrease in the paravertebral disc height. In this case it may be desirable to join the related vertebral segments together by means of fusion. When fusion is to be performed, an interbody fusion device is positioned in said space such that it will maintain paravertebral height after discectomy. These devices are also referred to as vertebral cages.

Today, many of the cages used for filling the space between two vertebrae are not capable of expanding. In case of placing a cage that is not capable of expanding between the vertebrae, one of the cages having a standard height is placed by medium fit in accordance with a predetermined size, or the decision made during the surgery. This, in turn, makes it difficult to adjust paravertebral height. If the height of the cage is too much, two neighboring vertebrae may be spaced apart more than needed; or in the reverse situation, they may become loose in place. In the expandable systems, on the other hand, the expansion takes place over a side of the cage. The heights of the parallel surfaces of the cage contacting with the endplates change conically, but not in parallel, subsequent to expansion.

OBJECTS OF THE INVENTION

The object of the invention is to provide an expandable cage which is moveable by means of a balloon in order to close an opening which occurs between two vertebrae, when preferred.

The object of the present invention is to provide an expandable cage which has a unilateral movement and eliminates such incidences as dislocation and slippage between two vertebrae.

Another object of the invention is to provide an expandable cage the movement amount of which is controllable by means of a balloon.

DETAILED DESCRIPTION OF THE INVENTION

The expandable cage provided in order to achieve the object of the invention is illustrated in the accompanying figures, in which.

Figure 1:
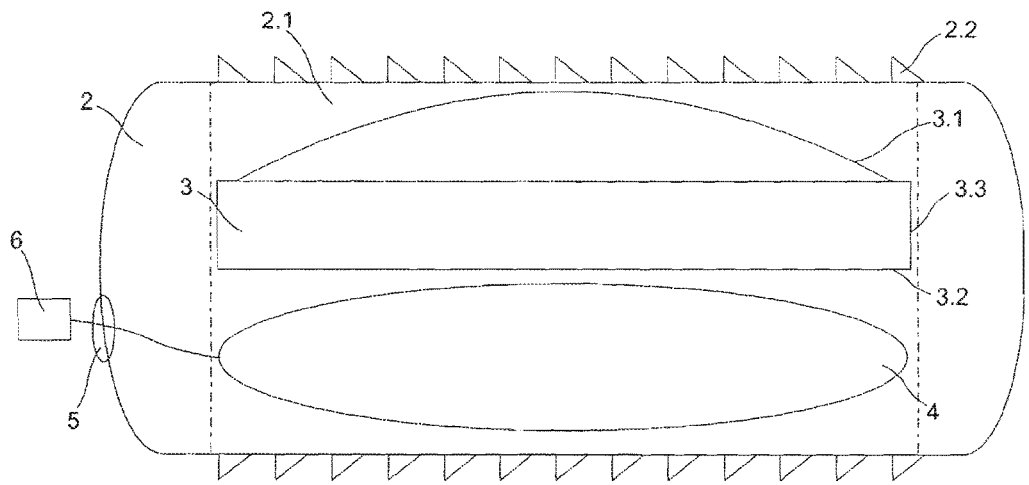
FIG. 1 is the schematic view of the expandable cage in unexpanded state.
Figure 2:
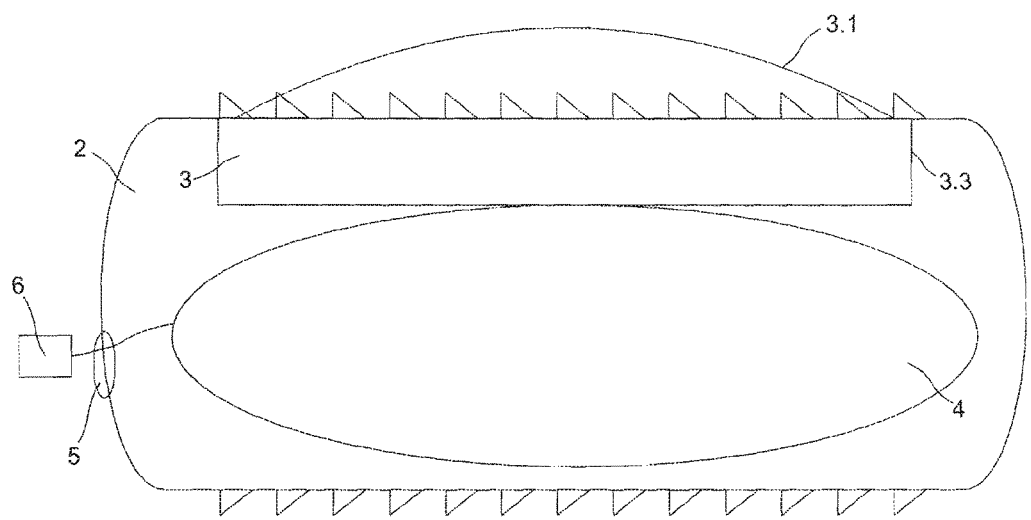
FIG. 2 is the schematic view of the expandable cage in expanded state.

The parts in the figures are numbered individually and the references corresponding to the related part are listed below.
1. Expandable cage
2. Body
   21. Space
   22. Rib
3. Moveable part
   31. Bearing area
   32. Base
   33. Nail
4. Balloon
5. Hole
6. Compression element An expandable cage (1) which is placed between vertebrae, is moveable when preferred, closes the opening between vertebrae upon being moved, and hence can be integrated in any intervertebral opening mainly comprises the following;
- at least one body (2) comprising at least one space (21) and rib (22),
- at least one moveable part (3) positioned in the body (2) and has a bearing area (31), a base (32), and at least one nail (33),
- at least one balloon (4) which applies the required force to the moveable part (3) such that the moveable part (3) will move unilaterally,
- at least one hole (5) made in the body (2) in a way to allow directing the balloon (4) into the space (21), and
- at least one compression element (6) to supply the required fluid into the balloon (4).

In one embodiment of the invention, the expandable cage (1) has a body (2). The body (2) closes, i.e. compensates, the opening between two vertebrae. The body (2) has a geometry and size such that it will be placed between two vertebrae. The body (2) is made of a biocompatible material. There exists a space (21) on the body (2). In an embodiment of the invention, the space (21) has a configuration expanding from the center, to the edges of the body (2). The space (21) may have the preferred geometry. In an embodiment of the invention, the space (21) has the same/similar geometry as/to the body (2). The depth of the space (21) is more or less the same as the height of body (2). The moveable part (3), which is to move towards the upper vertebra, is placed into the space (21). There exists ribs (22) on the surfaces of the body (2) contacting the vertebrae. Said rib (22) enables the body (2) placed between the vertebrae to firmly hold on to the vertebrae. Thanks to the rib (22), it is ensured that the body (2) placed between the vertebrae does not move between the vertebrae, or do not slip between the vertebrae.

In an embodiment of the invention, a moveable part (2) is provided in the space (21) within the body (2). The moveable part (3) is arranged in the space (21) provided in the preferred area of the body (2). The moveable part (3) is raised inside the expandable cage (1) by being moved by means of the balloon (4) in case an opening occurs between two vertebrae. The movement of the moveable part (3) is a unilateral movement. In an embodiment of the invention, the moveable part (3) moves upward from the bottom. The moveable part (3) may have the preferred geometry. A bearing area (31) is provided in the portion of the moveable part (3) facing the upper vertebrae. Bearing area (31) is the surface where the moveable part (3) moved by the balloon (8) contacts with the endplate of the upper vertebra in case said bearing area is preferred to be moved. The bearing area (31) has virtually the same geometry as the endplate of the vertebra. Thus, in case the moveable part (3) contacts with the endplate of the vertebra, said two surfaces fit properly in one another, i.e. one surface fits perfectly in the other. A base (32) is provided in the portion of the moveable part (3) facing the lower vertebrae. Said base (32) is the surface where the moveable part (3) contacts with the balloon (4) in case a balloon (4) is used. The base (32) may have the preferred geometry. There exist nails (33) in the portions of the moveable part (3) which contact with the space (21). These nails (33) restrict downward movement of the moveable part (3) and once the latter is raised inside the body (2), thereby ensuring a firm hold.

An embodiment of the invention comprises a balloon (4). The balloon (4) is located under the base (32) of the moveable part (3) in the preferred state. Thanks to said balloon (4), the moveable part (3) can raise inside the body (2). A fluid is compressed into the balloon (4), whereby the balloon (4) is inflated. As the balloon (4) inflates, the moveable part (3) moves unilaterally inside the body (2).

In an embodiment of the invention, the body (2) is provided thereon with a hole (5). This hole (5) is made in order to allow the access of the balloon (4) to the space (21) within the body (2). In the preferred state, the balloon (4) is made to pass through the hole (5) and is inflated, and thus it enables the moveable part (3) to move inside the body (2). After this procedure is completed, the balloon (4) is withdrawn from the hole (5) and removed through the space (21). The hole (5) disposed on the body (2) and allowing access of the balloon (4) to the space (21) within the body (2) may have a preferred geometry. Said hole (5) is preferably of a geometry and size such that the balloon (4) will pass therethrough.

An embodiment of the invention comprises a compression element (6). The compression element (6) serves for compressing a fluid into the balloon (4). Thus, the balloon (4) is inflated by means of the compression element (6), thereby ensuring the movement of the moveable part (3) inside the body (2) towards the upper vertebra.

The expandable cage (I) according to the invention has a body (2). The body (2) is properly fitted between two vertebrae thanks to the ribs (22) provided thereon. There exists a space (21) in the middle portion of the body (2). The moveable part (3) is arranged inside the space (21). In case an opening that cannot be compensated by the body (2) occurs between the two vertebrae, the balloon (4) is passed through the hole (5) provided on the body (2). The balloon (4) is located under the base (32) of the moveable part (3). Said balloon (4) is connected to the compression element (6). In case it is preferred that the moveable part (3) is moved in one direction, a fluid is compressed into the balloon (4) by means of the compression element (6). The balloon (4) inflated by the fluid compressed by means of the compression element (6) makes the moveable part (3) move towards the upper vertebra in the preferred height. When the movement of the moveable part (3) is ceased, the opening which occurs between two vertebrae after inserting the expandable cage (I) will be compensated.

The invention claimed is:

1. An expandable cage for placement between two vertebrae so as to close an opening between the two vertebrae upon being moved, the expandable cage comprising:
   at least one body of a biocompatible material, the body having at least one space and at least one rib, the body adapted to be placed between the two vertebrae so as to close the space between the two vertebrae, the body having an upper end and a lower end;
   at least one moveable part positioned in the space of the body, the moveable part having a bearing area adapted to face an upper vertebrae of the two vertebrae, the moveable part having a base adapted to face a lower vertebrae of the two vertebrae, the bearing area having a geometry adapted to match a geometry of an end plate of the upper vertebrae, the movable part being movable within the space of the body between a retracted position and an extended position, the bearing area positioned inwardly of the upper end of the body when in the retracted position, the bearing area having a portion extending outwardly of the upper end of the body when in the extended position and adapted to be in surface-to-surface relationship with the upper vertebrae when in the extended position, at least one nail extending through a wall of the body and engaging the movable part so as to fix the movable part in the extended position;
   at least one balloon being inflatable so as to apply a force to the moveable part so as to move the moveable part unilaterally from the retracted position to the extended position, the balloon being deflatable and withdrawable through a hole formed in the body; and
   at least one compression element cooperative with the balloon so as to compress a fluid into the balloon so as inflate the balloon so as to move the moveable part from the retracted position to the extended position.

2. The expandable cage of claim 1, the moveable part adapted to be moved by the balloon so as to raise in the space so as to close an opening between the two vertebrae.

3. The expandable cage of claim 1, wherein the bearing area is adapted to fit properly in an end position of the upper vertebrae.

4. The expandable cage of claim 1, wherein the balloon is positioned under the base of the movable part.

5. The expandable cage of claim 1, the balloon being insertable through the hole and into the body.

* * * * *